United States Patent
Hughes et al.

(10) Patent No.: US 6,770,051 B2
(45) Date of Patent: Aug. 3, 2004

(54) SUSPENSION DEVICE AND METHOD

(75) Inventors: Michael Scott Hughes, Glencoe, MO (US); William Hagen, Simpsonville, SC (US); Brian Doty, St. Peters, MO (US); Gordon Persaud, Lee's Summit, MO (US)

(73) Assignee: Mallinckrodt Inc., St. Louis, MO (US)

( * ) Notice: Subject to any disclaimer, the term of this patent is extended or adjusted under 35 U.S.C. 154(b) by 90 days.

(21) Appl. No.: 09/918,240

(22) Filed: Jul. 30, 2001

(65) Prior Publication Data

US 2001/0056256 A1 Dec. 27, 2001

Related U.S. Application Data

(63) Continuation-in-part of application No. 09/513,087, filed on Feb. 25, 2000, and a continuation of application No. PCT/US00/13905, filed on May 19, 2000, which is a continuation-in-part of application No. 09/316,315, filed on May 21, 1999, now Pat. No. 6,554,792.

(51) Int. Cl.⁷ ............................................. A61M 37/00
(52) U.S. Cl. ........................................ 604/85; 600/420
(58) Field of Search ........................... 604/82–85, 87, 604/92, 93.01, 131, 140, 50, 181, 183, 187, 218; 600/300, 407, 410, 419–420, 427, 431, 432, 437, 458; 222/145.1, 145.5, 326, 386; 424/9.5, 9.52

(56) References Cited

U.S. PATENT DOCUMENTS

| | | | |
|---|---|---|---|
| 3,302,834 A | 2/1967 | Alsop | 222/162 |
| 3,470,874 A | 10/1969 | Accetta | 128/173.1 |
| 3,472,455 A | 10/1969 | Johnson et al. | 239/135 |
| 4,030,665 A | 6/1977 | Koyama | 239/373 |
| 4,596,555 A | 6/1986 | Theeuwes | 604/56 |
| 5,030,203 A | 7/1991 | Wolf, Jr. et al. | 604/85 |
| 5,310,540 A | 5/1994 | Giddey et al. | 424/9 |
| 5,318,539 A | 6/1994 | O'Neil | 604/118 |
| 5,328,099 A | 7/1994 | Petit et al. | 239/372 |
| 5,470,311 A | 11/1995 | Setterstrom et al. | 604/24 |
| 5,505,193 A | 4/1996 | Ballini et al. | 128/200.15 |
| 5,520,166 A | 5/1996 | Ritson et al. | 128/200.14 |
| 5,522,378 A | 6/1996 | Ritson et al. | 128/200.14 |
| 5,569,191 A | 10/1996 | Meyer | 604/82 |
| 5,660,167 A | 8/1997 | Ryder | 128/200.21 |
| 5,695,741 A | 12/1997 | Schutt et al. | 424/9.52 |
| 5,720,938 A | 2/1998 | Schutt et al. | 424/9.51 |
| 5,806,519 A | 9/1998 | Evans, III et al. | 128/654 |
| 5,897,530 A * | 4/1999 | Jackson | 604/132 |
| 5,897,851 A | 4/1999 | Quay et al. | 424/9.52 |
| 5,935,113 A * | 8/1999 | Dysarz | 604/263 |
| 5,985,246 A | 11/1999 | Unger | 424/9.51 |
| 6,006,745 A | 12/1999 | Marecki | 128/200.23 |
| 6,235,003 B1 * | 5/2001 | Dysarz | 604/195 |

FOREIGN PATENT DOCUMENTS

| | | | |
|---|---|---|---|
| DE | 19625102 | 8/1997 | B01F/5/06 |
| EP | 0664136 | 7/1995 | A61M/5/28 |
| WO | WO9608227 | 3/1996 | |

* cited by examiner

*Primary Examiner*—Loan H. Thanh
(74) *Attorney, Agent, or Firm*—Wood, Herron & Evans, L.L.P.

(57) ABSTRACT

A device and method for providing a suspended agent such as a contrast agent without mechanical resuspension. A volume of agent (12) is divided into sub-volumes in a network (8) of tubes (18), cells (42), sponges (44), grooves (48), etc. A propellant fluid (16) flows through the network (8) to release the suspended agent (12). The network (8) may be internal to a container (10) for the propellant fluid (16). Alternatively, the network (8) may be adjacent an exit port (24) of a container (10) for the propellant fluid (16), or may be in-line between a propellant fluid container (10) and a patient. The invention reduces sedimentation of agents into one or a few aggregates and eliminates a mechanical mixing step. The invention thus provides a uniformly suspended agent, improving patient health and safety and increasing cost and time savings.

6 Claims, 7 Drawing Sheets

SUSPENSION DEVICE AND METHOD

CROSS REFERENCES TO RELATED APPLICATIONS

This application is a continuation-in-part of Application Ser. No. 09/513,087, filed Feb. 25, 2000, now pending, and is a continuation of PCT/US00/13905 filed May 19, 2000 which is a continuation-in-part of Application Ser. No. 09/316,315 filed May 21, 1999, now U.S. Pat. No. 6,554,792.

FIELD OF THE INVENTION

The invention relates to a device and method of using the device for providing a suspended volume of an agent without additional mixing.

BACKGROUND

Agents that do not persist in a suspended state and sediment must be resuspended prior to use. One example of an agent that must be resuspended prior to use is a pharmaceutical colloid, such as a contrast agent that is injected into a patient to enhance an imaging procedure. Contrast agents are used in various types of imaging including x-ray, magnetic resonance imaging (MRI), computed tomography (CT) and ultrasound (US). A contrast agent that comes out of suspension must be resuspended before placing the desired volume to be dosed into a delivery container such as a syringe. If there is a delay before the dose is injected into a patient, for example while preparing the patient or equipment, or if the infusion is extended, the agent must again be suspended before or during administration.

Resuspension of contrast agent requires mechanical manipulations, for example, removing a filled syringe positioned in an injector and remixing its contents. Additional remixing steps may delay a critical infusion time or, if remixing is omitted, the entire imaging procedure may have to be repeated due to suboptimal contrast obtained. Duplicate procedures not only put patients at increased risk and inconvenience, but are also cost- and time-inefficient. Even if the need to resuspend a single bolus injection is not prohibitive for a given procedure, repeated bolus injections or long term continuous infusions can become problematic due to the agent coming out of suspension during administration.

The loss of suspension for a contrast agent at any point in a delivery system to a patient, such as in a syringe and/or in the connecting tubing, severely limits the duration of continuous infusions or the time between intermittent injections. The need to initially resuspend the colloid or other type of agent, and to further suspend if the agent is not used shortly after resuspension, requires either time-consuming effort and vigilance by the user or the use of mechanical mixing devices. In any case, the need to resuspend an agent poses an additional step and a possible source of error in an imaging procedure.

SUMMARY OF THE INVENTION

The invention is directed to a method to control the rate at which a volume of an agent suspended in a fluid is delivered to a patient. The agent, provided in a device having a tubular network and inflow and outflow ports for a fluid to propel the agent, is divided into sub-volumes within the tubular network. By altering the flow to which the agent is exposed, for example, a laminar or nonlaminar flow, the rate at which the fluid is delivered is controlled. For example, laminar flow may be altered by changing the density, cross-sectional diameter, length, and/or pitch of the tubular network, and/or by symmetrically or randomly altering the radius of curvature. For example, the radius of curvature and/or density from the inflow port to the center of the device may progressively decrease, and the radius of curvature and/or density from the center of the device to the outflow port may progressively increase. Non-laminar flow may be altered by replacing a circular internal geometry of the tubular network with a non-circular geometry, in a symmetric or random manner and along part of or along the entire network path.

The invention is also directed to a method to control the rate at which a volume of an agent suspended in a fluid is delivered to a patient by providing the agent in a device having a tubular network containing sub-volumes of the agent. The device also contains inflow and outflow ports for fluid to propel agent from the network. The rate is controlled by altering a laminar flow of agent through the network by altering the network density, or by altering a nonlaminar flow of agent through the network by replacing a circular internal geometry of a network path with a non-circular geometry.

The invention is also directed to a suspension device that contains a tubular network providing at least one network path and containing sub-volumes of the agent, and has inflow and outflow ports for a fluid to propel agent from the network. The device has a cross-sectional internal geometrical configuration that may be of geometric shape and may be contiguous, non-contiguous, symmetrical or non-symmetrical along the length of the network. The tubular network may have a symmetrically altered radius of curvature, for example, the radius of curvature may increase from an inflow port to the center of the device and may decrease from the center of the device to an outflow port. The tubular network may be a compressible helix, either housed within a container such as a syringe or a network support, or placed in-line. The device may control the rate of agent delivery to a patient, and/or may enhance mixing of the agent.

The invention is also directed to a method and apparatus of decreasing escape of a gaseous agent contained within a suspension device, where the device is a network to contain sub-volumes of the agent and has inflow and outflow ports for a fluid to propel the agent from the network. In the method, one or more devices is provided within a container that is less permeable to the gaseous agent than the network. The apparatus is a container made of a material such as glass or a thick walled plastic such as polyvinyl chloride (PVC) or polypropylene that is less permeable to the gaseous agent than the network.

The invention is also directed to a suspension device for a volume of an agent that is a tubular network arranged in at least two parallel columns, where each column is independently operatively connected and contains sub-volumes of the agent, and inflow and outflow ports for a fluid to propel agent from the network. This embodiment of the device permits the user to adjust the network volume.

The invention is also directed to a method to deliver an agent that contains microbubbles of a pre-determined size. The agent is contained in a suspension device having a tubular network that contains sub-volumes of the agent, and inflow and outflow ports for a fluid to propel agent from the network. In the method, a force exerted on the microbubble-containing agent is altered by exposing the agent to a non-circular internal network geometry.

The invention is also directed to a method to alter a size distribution of microbubbles in a contrast agent injected into a patient by altering a flow rate of the agent between the agent source and an inflow line into the patient.

The invention is also directed to a suspension device for a volume of a contrast imaging agent, such as a microbubble-containing agent. The device is a compressible helical network, for example ½ foot to fifty feet in an uncompressed state, containing sub-volumes of the agent and with inflow and outflow ports for a fluid to propel agent from the network.

The invention is also directed to a method of providing a volume of a suspended agent to a patient by dividing the volume into sub-volumes, storing the sub-volumes in a network, mechanically mixing the agent in the network either before, during or after releasing the agent sub-volumes into a patient through a patient connector by providing a fluid under pressure through the network to propel the suspended agent.

These and other embodiments will become apparent in light of the following figures and detailed description.

DETAILED DESCRIPTION

The device of the invention sub-divides a desired volume of an agent to suspend the agent without mechanical mixing. As used herein, the device is comprised of a network of structures for containing sub-volumes of the agent, with the entire volume of agent contained in the network component sub-volumes. Resuspension is caused by viscous fluid flow through the network of sub-volumes, turbulence promoted interlaminar mixing, and mixing caused by varying the gravitational orientation of agent sub-volumes. As will be described, the device may be located in the same container that contains propellant fluid to eject the agent from the network (container package embodiment). Alternatively, the device may be located adjacent an exit port of a propellant fluid container (add-on embodiment), or may be positioned in-line at any point in a fluid path between the propellant fluid container and the ultimate deposit site such as a patient (in-line embodiment). As used herein, a propellant fluid is one that is used to eject the agent from the network of tubes, cells, etc. As used herein, a network is defined as a collection of structures which contain the entire desired volume of agent in sub-volumes in the device, and hence increase the surface area of the agent over which the propellant fluid must flow, In one embodiment, the network has a common exit port, and agent sub-volumes are ejected from the network at a substantially equal rate. The network may encompass tubes, cells, sponges, etc. and is not limited by volume or configuration.

The device sub-divides a volume of an agent to prevent it from settling or sedimenting into one or a few dense aggregates without the need for mechanical mixing or suspending prior to use, and thus reduces or eliminates the problem of remixing or resuspending an agent that has come out of suspension prior to use. Use may be either preparing an injection dose by transferring the desired volume of agent from a package to a dosing container such as syringe, or injecting the dosing volume of agent into a patient. This problem may occur with contrast agents, either while in their package or portioned in a container such as a syringe for injecting into a patient about to undergo an imaging procedure. The invention solves the problem by sub-dividing the volume of the agent to prevent separation or aggregation of the agent from the suspending liquid and by turbulence or gravitationally promoted interlaminar mixing. While mechanical mixing is not required, it may be used with the inventive device either before, during, or after mixing in the device, to supplement mixing achieved by the device.

Dividing a uniformly suspended contrast agent or other agent into a network of sub-volumes rather than a single large volume inhibits the particles from either floating or precipitating into one or more larger masses or aggregates. The invention thus reduces or obviates the need for mixing before or during a process, such as an infusion process. This increases the quality, safety, and cost- and time-efficiencies of the process.

Figure 1:
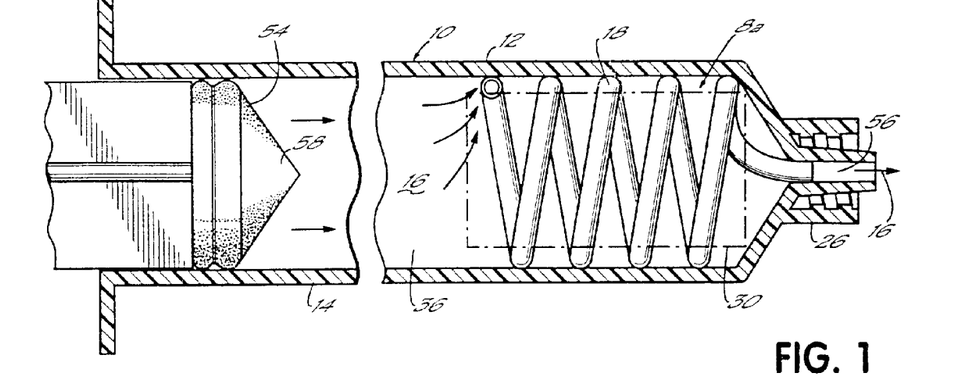
FIG. 1 is a cross-sectional view of a syringe container with an internal tubular network.

With reference to FIG. 1, a network 8a containing divided sub-volumes of an agent 12 is internal to a container 10 for propellant fluid 16. The container 10 may be a syringe 14 or other types of containers which include but are not limited to vials, bags having flexible or semi-flexible walls, bottles of either glass or plastic, etc. The agent 12 contained in the network 8a is ejected from the container 10 as propellant fluid 16 flows through the network 8a and displaces the agent 12. The propellant fluid 16 is any viscous fluid (liquid or gas) that is biocompatible. The propellant fluid may be a diluent for the agent 12 such as normal saline, water, buffer, etc. The propellant fluid 16 may also be a contrast agent that is different from the agent 12 injected for the imminent imaging procedure.

Figure 1A:
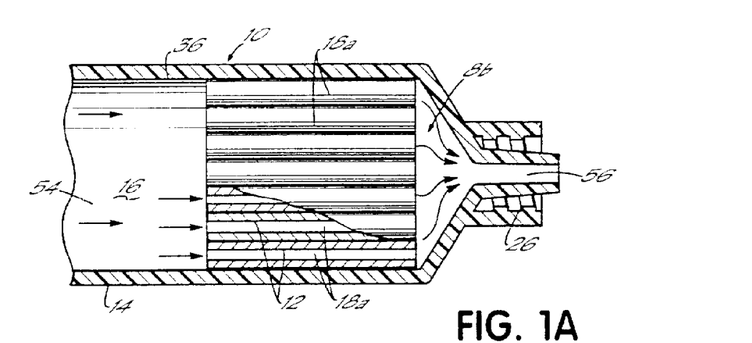
FIG. 1A is a view similar to FIG. 1 of an alternate embodiment of the invention.
Figure 2:
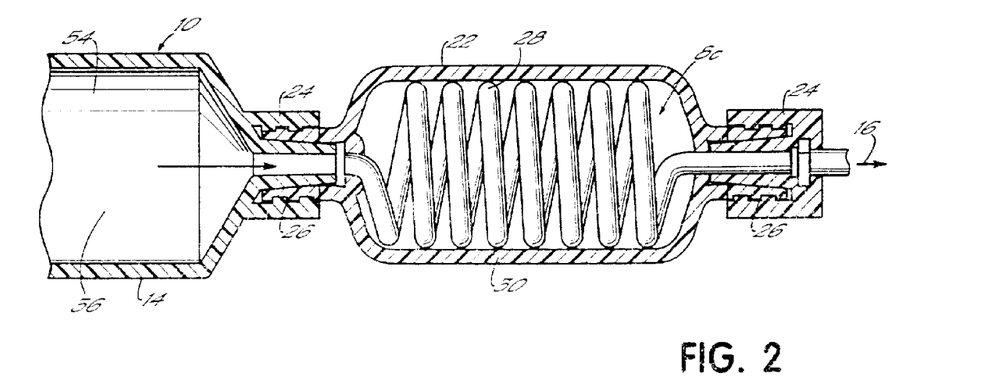
FIG. 2 is a cross-sectional view of a syringe container with an external tubular network operably attached to a propellant fluid container exit port.
Figure 3:
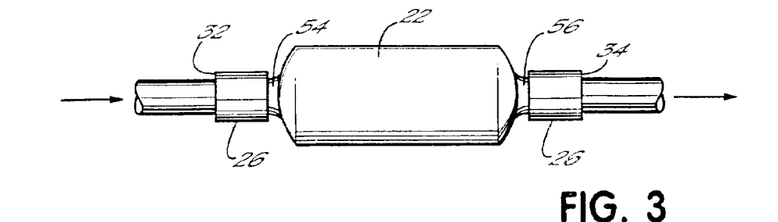
FIG. 3 is an elevational view of an in-line device.
Figure 4A:
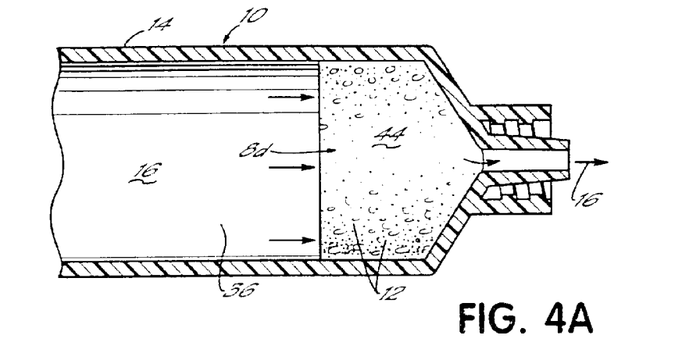
FIGS. 4A, 4B and 4C are various network embodiments and configurations.
Figure 4B:
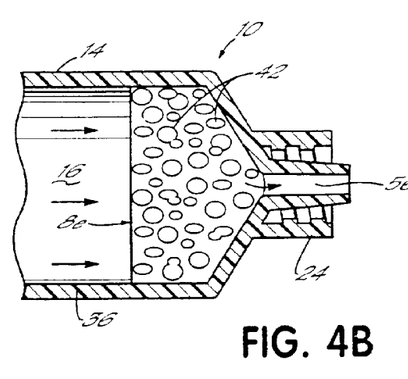
Figure 4C:
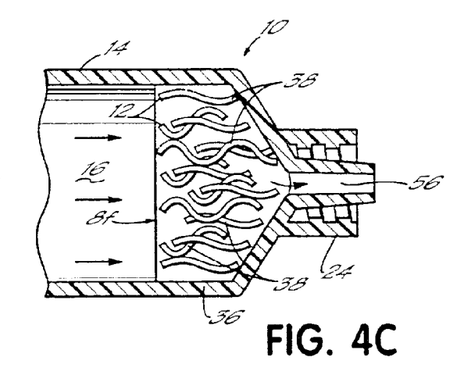

The network 8a may be any structure that serves to contain a sub-volume of the desired total volume of an agent 12 in a unit area. The network 8a may be contained in a network holder 22 (FIGS. 2 and 3). The network 8a may be tubes 18 which, as used herein, encompass tubules, microtubules, channels, or other types of hollow cylinders that convey a fluid or that function as a passageway, whereby a volume of agent 12 is divided into sub-volumes of any size. There are numerous configurations of the tubes 18 that can be used to sub-divide the volume of agent 12. These include, but are not limited to, a single long tube 18 as best shown in FIG. 1 or a collection of tubes 18a as shown in FIG. 1A. The tubes 18 may be in any configuration, such as one or more coils or helices, an angular or stairstep configuration, and/or even random configurations. A collection of tubes 18 may similarly be one or more coils or helices, an angular or stairstep configuration, and/or even random configurations, or may be arranged in a parallel configuration (FIG. 1A). The geometries and configurations of the network 8 may be combined in either regular or random configurations. While FIGS. 1 and 1A show tubes 18 positioned in a syringe 14 without any accompanying support, other configurations are contemplated. For example, the tubes 18 may be positioned within a network holder 22 (FIGS. 2 and 3), or may be supported or held in a syringe 14 or network holder 22 by a fixture such as 24 (shown in phantom lines in FIG. 1) which may extend for part of or all of the length of the network 8.

With reference to FIG. 2, a dose delivery container 10 that is a syringe 14 is shown with a network holder 22 containing the network 8 external to the syringe 14. The network 8c is packaged within a network holder 22, which may be any container in which the network is housed or retained and may be made of any biocompatible material. The network holder 22 containing the network 8c may be separable from the syringe 14 or other container 10 and attached to an exit port 24 of the syringe 14 or container 10. The network holder 22 for the network 8c may also be manufactured as part of the container 10, which may be useful as a pre-packaged embodiment of the invention. In a non-pre-packaged embodiment, the network holder 22 may be attached to an exit port 24 using, for example, connectors 26 such as luer fittings. The exit port 24 of the syringe 14 may be fitted with luer fittings, such as Luer-Lok® caps (Becton-Dickinson), or may have luer fittings such as metal, brass or glass luer tips attached. As previously described, a support or fixture 30 for the tubes 28 may be used, and the support 30 and tubes 28 may be contained in a network holder 22. As one alternative, the support 30 and tubes 28 may be contained directly in the container 10. As another alternative, the tubes 28 in a network holder 22 may be unsupported as shown in FIG. 2.

While FIG. 2 illustrates a network holder 22 which is attached to a syringe 14, other embodiments are contemplated. With reference to FIG. 3, the network (not shown) contained in a network holder 22 is shown in an in-line embodiment. The network holder 22 is fashioned with connectors 26 at both an inflow port 32 and an outflow port 34. Tubing is connected to connectors 26 to carry propellant fluid 16 from a syringe to holder 22 and from holder 22 to a patient. The connectors 26 may be the same or different at the inflow 32 and outflow 34 ports and may be any type such as luer fittings, as previously described. Network holder 22 and the network inside may be configured symmetrically, so that the orientation of the network holder 22 in an in-flow embodiment need not be a concern; i.e., there is no back-to-front or front-to-back limitation. Agent 12 can be removed from the network within the network holder 22 upon pressure from a propellant fluid 16.

A network 8 that is internal to a container 10 such as a syringe 14 need not be housed in a network holder 22. As seen in FIGS. 1 and 1A, the network 8a, 8b of tubes 18 or other structures may be positioned directly within the barrel 36 of the syringe 14. In an alternative embodiment, the network 8 that is internal to a syringe 14 or other container 10 may also be housed in a network holder 22. In either embodiment, the barrel 36 of the syringe 14 may contain a propellant fluid 16 that, upon initiation of flow, provides pressure to release or eject the agent 12 from the network 8. The propellant fluid 16 need not be prefilled in the barrel 36 of the syringe 14, but instead may be added to the barrel 36 of the syringe 14.

Figure 12A:
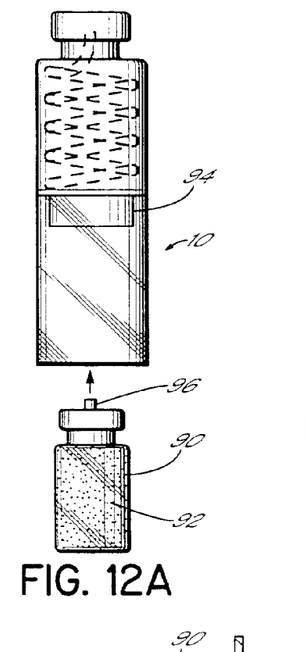
FIGS. 12A, 12B, and 12C show a self-activation and discharge device.
Figure 12B:
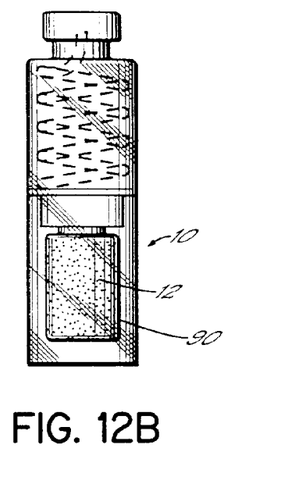
Figure 12C:
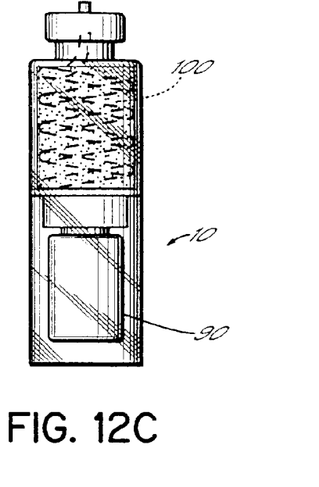

In one embodiment and with reference to FIGS. 12A–C, a fluid 92 that is used to propel the agent through the network (not shown) may be contained within the same container 10 as that which contains the network 8. Thus, the embodiment would be a self-contained, combined storage container 10 and delivery device. This would eliminate the need for transferring the agent 12 into a separate delivery device, such as a syringe 14. Use of this embodiment would permit delivery of a uniformly suspended agent 12, without the need for either manual or mechanical mixing, from the same container 10 in which the agent 12 was stored. The embodiment thus provides activation and delivery, in the case where the agent is a microsphere or microbubble formulation of the agent and activation is required to form the microspheres or microbubbles, or delivery of a stable, uniformly suspended agent 12 from its original storage container 10 using a simple hand-held one-step device.

Contrast agents, as used for ultrasound and other imaging modalities, may be comprised of microbubbles or microspheres that contain air or an inert gas or liquid emulsion. These gases or liquids provide echogenicity and a means for visualization of anatomical regions. The size of the bubbles or spheres formed is an important parameter in the efficacy and safety of the product. The bubble or sphere size is dependent upon formulation components, methods of manufacture, stability, etc.

Formulations are prone to stability problems when packaged into vials due to destabilization of the bubbles or spheres or breakdown of key components, making it difficult to generate bubbles or spheres by hand agitation. Often, hand agitation may not be significant enough to produce consistent and efficacious bubbles or spheres. The invention provides for one step hand activation without the need for an instrument (such as a shaker or agitator), as the resulting product is ready to use after activation.

Among the advantages to the above-described apparatus are that the dispersion is generated immediately before use. Particularly with respect to contrast agents, where persistence size of bubbles are limiting factors and provide a diagnostic advantage, increasing bubble persistence and uniform desired size as near to the time and site of infusion as possible is desirable. The above-described system also limits the exposure time of the components, allowing components that are less than optimally compatible to be used. It also enhances stability of the agent due to the package design, for example, transfer to a separate container is not necessary. Ingredients which otherwise would be incompatible for an extended time prior to administration may be mixed, as only short-term exposure exists prior to use. The method facilitates high pressure in situ mixing, and affords flexibility in the formulation design, since only a limited stability is needed.

The bubbles or spheres generated are microfine and monodispersed. Bubble aggregation, which may be problematic, is thereby minimized. The bubbles generated using the inventive device and method are of a uniform, small size, providing for enhanced imaging. In one embodiment, one or more screening devices, such as filters or wire mesh screens, may additionally be incorporated within the device to select bubbles within a certain size range for administration. Furthermore, the inventive method accomplishes all of this without resorting to extra processing steps, as occurs with lyophilization.

A storage container 10, such as a vial, containing the agent 12 to be delivered is adapted to receive a charging container 90 to generate an aerosol formulation 100 on FIG. 12A of the agent 12, similar to shaving cream. For example, a storage container 10 has a receiving port 94 for an engaging member 96 on the charging container 90. The charging container 90 contains a pressurized fluid 92 such as an inert gas (including, but not limited to, hydrogen, nitrogen, helium, and argon), or another type of formulation (for example, octafluoropropane ($C_3F_8$), oxygen, carbon dioxide, etc.). The fluid 92 is activated and depressurized when the engaging member 96 is connected with the receiving port 94 (e.g., by breaking a seal). The apparatus also contains a compartment into which the charged agent mixes with the agent to be delivered (expansion container).

Activation is achieved by operatively attaching the charging container 90 to the storage container 10 via the receiving port 94 (e.g., applying pressure sufficient to break a seal FIG. 12B). The gas or other formulation 92 contained in the charging container 90 is thereby discharged into the storage container 10 FIG. 12C, the agent 12 contained in the network (not shown) is propelled and mixed with the gas in the expansion chamber, and a uniform suspension of stabilized bubbles are available for infusion.

Figure 13A:
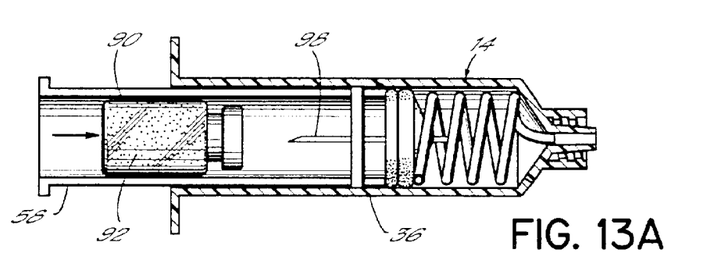
FIGS. 13A, 13B, and 13C show a self-activation and discharge syringe.
Figure 13B:
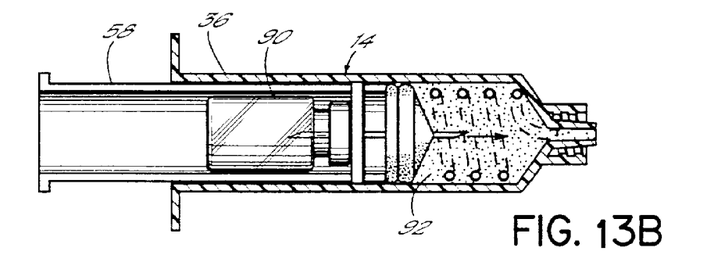
Figure 13C:
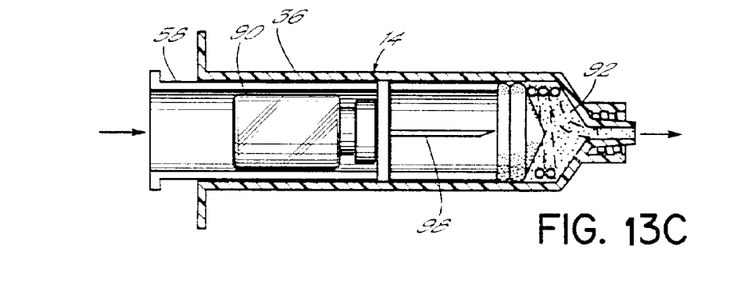

With reference to FIGS. 13A–C showing a syringe 14 delivery container 90, the charging container 90 is incorporated within the plunger 58 of the syringe 14. Application of pressure to the plunger 58 propels the agent contained therein. Advancement of the plunger 58 discharges the inert gas or other formulation 92 contained within the charging container 90 into the barrel 36 of the syringe 14 via contact with a means to pierce a receiving port (e.g., moving the container 90 past a piercing needle 98). A uniform dispersion thereby forms in the barrel of the syringe.

The sub-dividing volume structure of tubes 18 in the network 8 may assume a variety of geometries and configurations. As shown in FIGS. 1A, 2, 4A, 4B and 4C, the tubes 18 may be straight, coiled, helical, in random filaments 38, in an angular or stairstep (not shown) configuration, or may have other configurations. All of these alternatives are appropriate for use in any of the illustrated embodiments. The sub-dividing network 8 need not encompass tubes 18 at all; all shown in FIGS. 4A, 4B and 4C, the network 8d, 8e and 8f respectively, may be a series of discrete cells 42 (see FIG. 4B), or may have a sponge 44 type of structure (see FIG. 4A). In a cell 42 structure, the agent 12 is retained in or on discreet cells 42. In a sponge 44 structure, the agent 12 is either absorbed in or adsorbed on the sponge 44, rather than contained within tubes 18 or cells 42. A cell 42 or sponge 44 structure may also be used effectively in a network holder 22 separate from a syringe 14. In any embodiment, the network 8 may be configured so that there is a non-uniform direction for all sub-volumes, that is, there is no single upward, downward or lateral direction for all sub-volumes.

Figure 5:
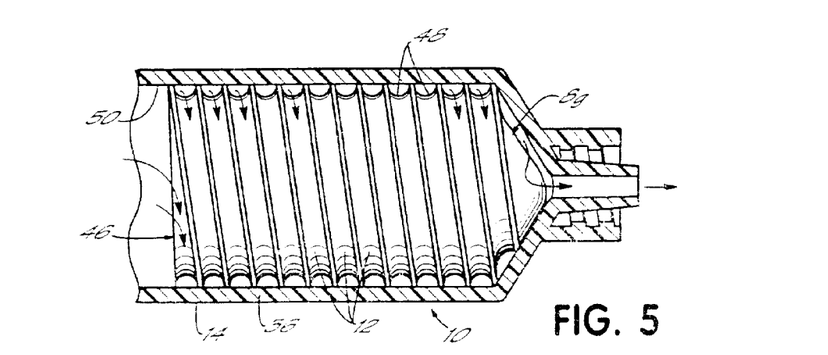
FIG. 5 is a cross-sectional view of a syringe container having an integral network.
Figure 6:
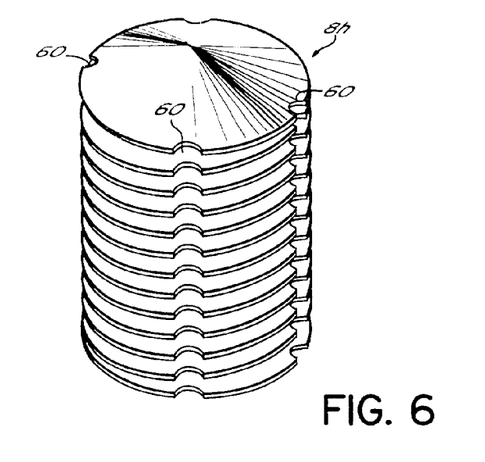
FIG. 6 is a cross-sectional view of an integral network with channels.

With reference to FIG. 5, a network 8g that is integral with the container 10 is shown. In this embodiment, the network 8g is fabricated as grooves or channels 48 that are etched or otherwise manufactured within the container 10 itself. For example, a syringe 14 may have a cylindrical plug 46 disposed in the barrel 36, where the plug 46 has parallel or spiral grooves 48 in its outer surface. The grooves 48 contain the agent 12 between the syringe 14 inner wall 50 and barrel 36. As shown in FIG. 6, the grooves 48 may contain substantially perpendicular channels 60 at one or more regularly spaced intervals. The channels 60 permit rapid and uniform filling of the network 8 with agent 12 added into one side of a container 10 when the other side of the container 10 is sealed. In another embodiment, the syringe 14 has a cylindrical plug 46 disposed in the barrel 36 as previously described, where the inner wall 50 of the syringe 14 has parallel or spiral grooves in its structure. The grooved structures 48 may also be used in a separate network holder 22. In these embodiments, the grooved structure 48 comprises the network 8 which sub-divides the volume of agent 12. It will thus be appreciated that the network 8 may assume a variety of forms and configurations whereby a volume of agent 12 can be sub-divided into smaller volumes with increased surface area of the agent 12 over which the propellant fluid 16 flows to reduce sedimentation.

The network 8, whether in the form of tubes 18, cells 42 or sponges 44, may be made of any biocompatible material that can withstand sterilization and is inert with respect to the agent 12, the propellant fluid 16, and the container 10. Examples of such materials for a tubular 18 network include biocompatible tubing such as polyethylene, polypropylene, silicon, rubber, etc., for example, Tygon® tubing (halogenated vinyl plastic, Norton Plastics). Tubes 18 used in kidney dialysis devices, such as cellulose tubes 18 having a nominal diameter of 200 $\mu$m, may also be used in the invention. In a network 8e having cells or voids, the cells 42 may be produced by incomplete fusion of pieces of fusible material such as thermoplastics or metals. The cells 42 may be made of Delrin™, polycarbonate such as Lexan™, polyethylene, polypropylene, silicon, rubber, etc. In a network 8d having a sponge 44 structure, the sponge 44 may be made of porous Delrin™, porous polycarbonate such as Lexan™, porous polyethylene, porous polypropylene, porous silicon, porous rubber, etc.

The size and volume of the network 8, container 10, and network holder 22 may vary, depending upon a number of factors. These factors include the volume of agent 12, the size of the container 10, the duration of the imaging or other procedure to be performed, etc. There is neither a maximum nor a minimum volume for the network 8, container 10, or network holder 22, and an exponential range of volumes is contemplated by the invention. For embodiments in which the network 8 is internal or integral with the container 10, however, the volume of agent 12 contained within the network 8 is at most one-half the volume of propellant fluid 16 in the container 10. This ensures that substantially all the agent 12 will be released from the network 8 by the flow of propellant fluid 16. For example, volumes of contrast agent 12 injected for enhanced ultrasound imaging may range from 1 ml to about 10 ml. As an example, a 3 ml volume of agent would require using about a 10 ml syringe 14, with the tubular 18 or other structure of the network 8 containing 3 ml agent 12 and the remaining volume of the syringe 14 containing at least 3 ml, and more typically 4–5 ml, of propellant fluid 16. A 3 ml volume of agent 12 may be sub-divided in a syringe 14 having ten threads or grooves 48 per inch, with the threads or grooves 48 one millimeter deep, each thread or groove 48 containing about 0.3 ml agent 12.

The container 10 and/or network holder 22 may be manufactured having the network 8 preloaded with a uniformly mixed suspension of agent 12 such as a pharmaceutical colloid. The container 10 and/or network holder 22 may have both an entry port 54 and an exit port 56 with appropriate fittings 26 such as luer locks for connection to standard tubing or catheters, as is known to one skilled in the art (FIG. 3). To eject the agent 12 in the network 8 from the exit port 56 of the container 10 or network holder 22 and into the patient through a patient connector line, propellant fluid 16 may be injected into the entry port 54 or, alternatively, pressure may be applied to the propellant fluid 16 already in the container 10. The container 10 may also have a single exit port 56 and a plunger 58, with liquid 60 in the opposite end, to permit use as a prefilled syringe (FIG. 1).

The specific location, position and configuration of the network 8 may depend upon an intended use. For example, an agent containing a gas other than air should be housed in a container 10 that has been purged of air. A container 10 made of glass may be rendered air-tight more easily than a plastic syringe, and thus is preferable for this agent. Likewise, a network 8 that is internal rather than external is preferred for use with an agent that contains a gas other than air. This allows the propellant fluid 16 to be purged of air and become saturated with the agent-containing gas, maintaining a substantially anaerobic environment prior to injection.

One advantage of the invention is that it eliminates the need for resuspension of agents 12 that may come out of suspension, either in their original container 10 or in a dose delivery container such as a syringe 14. Conventional containers 10 require mechanical devices or manipulations to maintain colloids such as a contrast agent 12 in suspension. By eliminating the need for prior resuspension of the agent 12 for single-bolus injection, the device and method of the present invention provides a competitive advantage for injectable agents 12. In accordance with the principles of the present invention, a syringe 14 having a network 8 containing agent 12 can remain resuspendable for more than five months.

Maintaining the agent 12 in a substantially fully resuspendable state assures consistent quality and reduced sensitivity to user technique. The agent 12 may be shipped already prepackaged in the network 8. This arrangement has the potential to reduce susceptibility of agents, such as microbubble preparations, to mechanical vibration and shock which may decrease the integrity of the agent 12. Dividing the volume of agent 12 into sub-volumes also allows it to be more quickly preheated to a desired temperature, facilitating the efficiency of the entire imaging procedure.

Another advantage of the invention is that the colloid or other agent 12 may be released, ejected or expelled from the exit port 56 of the container 10 by injecting a propellant fluid 16. This precludes the need to draw the pharmaceutical or contrast agent 12 into a syringe 14 for injection, and provides similar advantages as enjoyed by pre-filled syringes.

Still another advantage of the invention is that, in those embodiments such as FIGS. 2 and 3 where network 8 is external to the syringe 14, the exit port 56 of the dose delivery container 10 or network holder 22 may be connected to a short angiocatheter (not shown) that is very close to a venous or arterial puncture site in a patient. This arrangement prevents loss of suspension of agent 12 that would occur inside a longer catheter, and permits use of a manual or power syringe located a substantial distance away from the patient, while preventing the need for the agent 12 to maintain resuspendable in the manual or power syringe 14 and connecting tubing. Instead, the manual or power syringe and tubing need only contain a non-colloidal fluid that does not require mixing or resuspending during long injection times.

A further advantage of the invention is realized with an optional built-in plunger 58 in the syringe 14. A built-in plunger 58 permits use of the device as a manual syringe 14 or with a small, battery-operated power injector at the end of a very short angiocatheter. In either case, the filled syringe 14 could be located very close to a venous or arterial puncture site, precluding the need to maintain the agent 12 resuspended in a long catheter for infusion into a patient. This embodiment also precludes the need for a fluid-filled syringe 14 connected to the entry port 54 of the dose delivery container 10 in order to eject the agent 12 from the exit port 56 of the dose delivery container 10.

Mixing of the agent 12 flowing through a network 8 having a tubular structure 18a–b, also called a tubular network 18, may be achieved by varying the intrinsic and/or extrinsic geometries of the tubes 18a–b. The effectiveness of mixing increases or decreases with alterations in the network cross-sectional geometry. Any change which increases flow velocity or turbulence will improve mixing. Since mixing of agent 12 can be accomplished by either turbulent flow (defined as the motion of a fluid having local velocities and pressures that fluctuate randomly) or non-turbulent (also called laminar) flow, providing configurations of tubes 18a–b that enhance either or both types of flow will promote mixing.

Interlaminar mixing may be promoted by altering the gravitational orientation of the agent 12 suspended as sub-volumes in the tubular network 18, or by altering turbulent flow. In an agent containing microbubbles, the agent may be thought of as being divided into sub-volumes which each contain a subset of the total number of microbubbles. Over short time intervals most of the microbubbles in a given sub-volume will tend to remain in the same sub-volume as agent flows through the network. As the various sub-volumes of agent flow through the network, the orientation will continuously vary between up and down as the sub-volume flows through the network. In effect, this results in the sub-volume being turned upside down, then downside up, then back to upside down, and so on. This mechanism promotes mixing of the microbubbles within a given sub-volume.

Figure 7A:
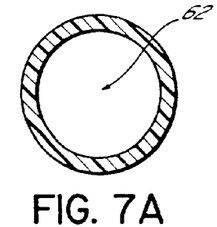
FIGS. 7A, 7B, 7C, 7D, 7E, 7F, 7G, 7H and 7I are embodiments of network cross-sectional geometries.
Figure 7B:
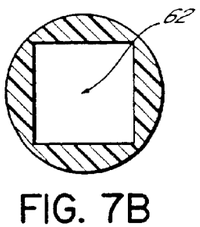
Figure 7C:
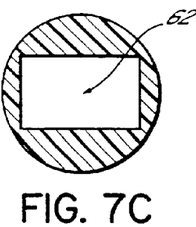
Figure 7D:
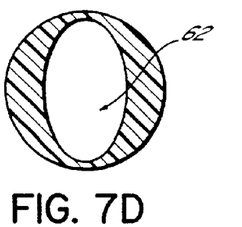
Figure 7E:
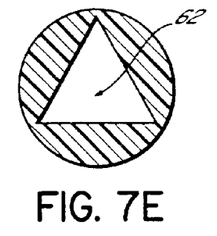
Figure 7F:
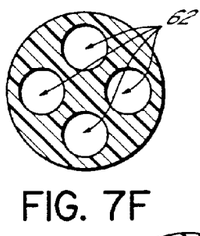
Figures 7G, 7H:
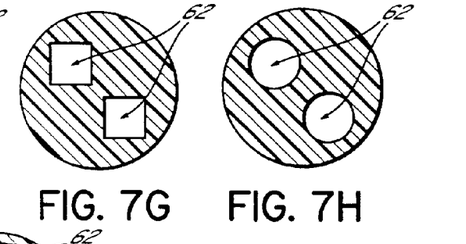
Figure 7I:
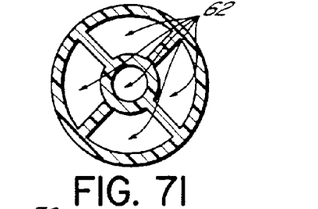

Turbulent flow may occur by exposing the agent 12 to one or a number of intrinsic geometries within the internal surface of the network. For example, and with reference to FIGS. 7A, 7B, 7C, 7D 7E, 7F, 7G, 7H, and 7I the geometry of the internal network path or channel 62 through which the agent 12 must pass in a tubular network 18 may be altered. The channel geometries 62 may be altered symmetrically at various points along the total length of the network 18a–b, or may be altered in a continuously variable or even random manner. The internal geometries 62 to which agent 12 is exposed may include, but are not limited to, single lumen channels that are circular FIG. 7A, square, FIG. 7B, rectangular FIG. 7C, elliptical FIG. 7D, triangular FIG. 7E, or other geometric shapes, multi-lumen channels that have a plurality of either the same or different geometric shapes such as a four lumen tube having circular channels FIG. 7F, a two lumen tube having circular FIG. 7G or square 7H channels, a five lumen tube having one inner circular lumen with four peripheral wedge-shaped lumens FIG. 7I, any combination or combinations of the above, or even random shapes, to promote the degree of mixing desired. For example, exposure to a channel geometry 62 that is square or rectangular creates increased mixing of the agent 12, compared to exposure to a channel geometry 62 that is circular or elliptical because a square channel exposes the flowing agent 12 to blunt edges, which in turn promotes turbulence. It will be appreciated that any geometric configuration and arrangement that will result in agitation or turbulence of the agent 12 as it flows through a channel 62 in a tubular network 18 is possible. The geometric type and/or length of tubes 18a–b containing a particular geometric type of channel will promote mixing of the agent 12 to different degrees, and may be selected according to the degree of mixing required. Single-lumen circular channels 62 have an internal channel diameter in the range of 0.005–0.1 inch. In one embodiment the circular internal diameter is 0.030 inch. In an alternate embodiment the circular internal diameter is 0.034 inch. Multi-lumen circular channels 62 have an internal channel 62 diameter in the range of 0.020–0.044 inch. Multi-lumen channels 62 may be arranged in any configuration and provide an advantage in being easier to fill with sub-volumes of agent, since a particular volume of agent 12 is divided into more than one tube. This also allows for a pro estimated. Glue is then applied to at least part of the adjacent helical surfaces to form a secure attachment. The user is then free to detach helices 106 as needed to provide additional length, if desired, or to secure additional helices 106 to minimize slack.

Figure 14A:
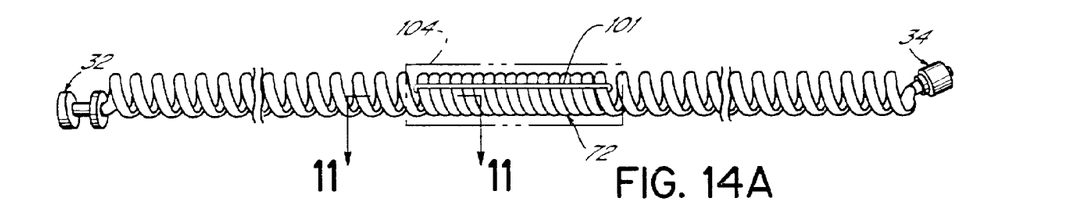
FIGS. 14A, 14B, and 14C show devices to minimize tangling of a network in a coiled helix embodiment.
Figure 14B:
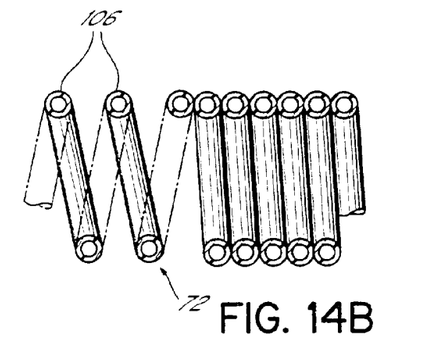
Figure 14C:
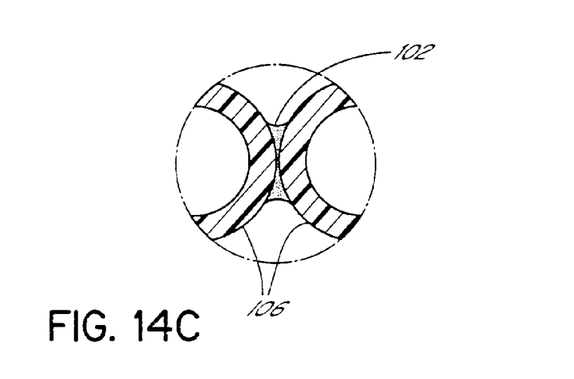

In an alternative embodiment, the coiled helix is secured using clamps 101 that are plastic. The clamps 101 may be adjustable or rigid, either in whole or in part. As one example, the terminal portions of the clamps 101 may be made of a rigid plastic, with the middle portions made of a resilient plastic to provide a spring-like action, akin to a spring-like toy. The user then adjusts the portion of the coiled helix 72 to be secured throughout use with the clamp 101 that is adjustable. As another example, the entire clamp 101 may be rigid, and the user would pre-select the portion of the coiled helix 72 to be either secured to unsecured during use.

Figure 11:
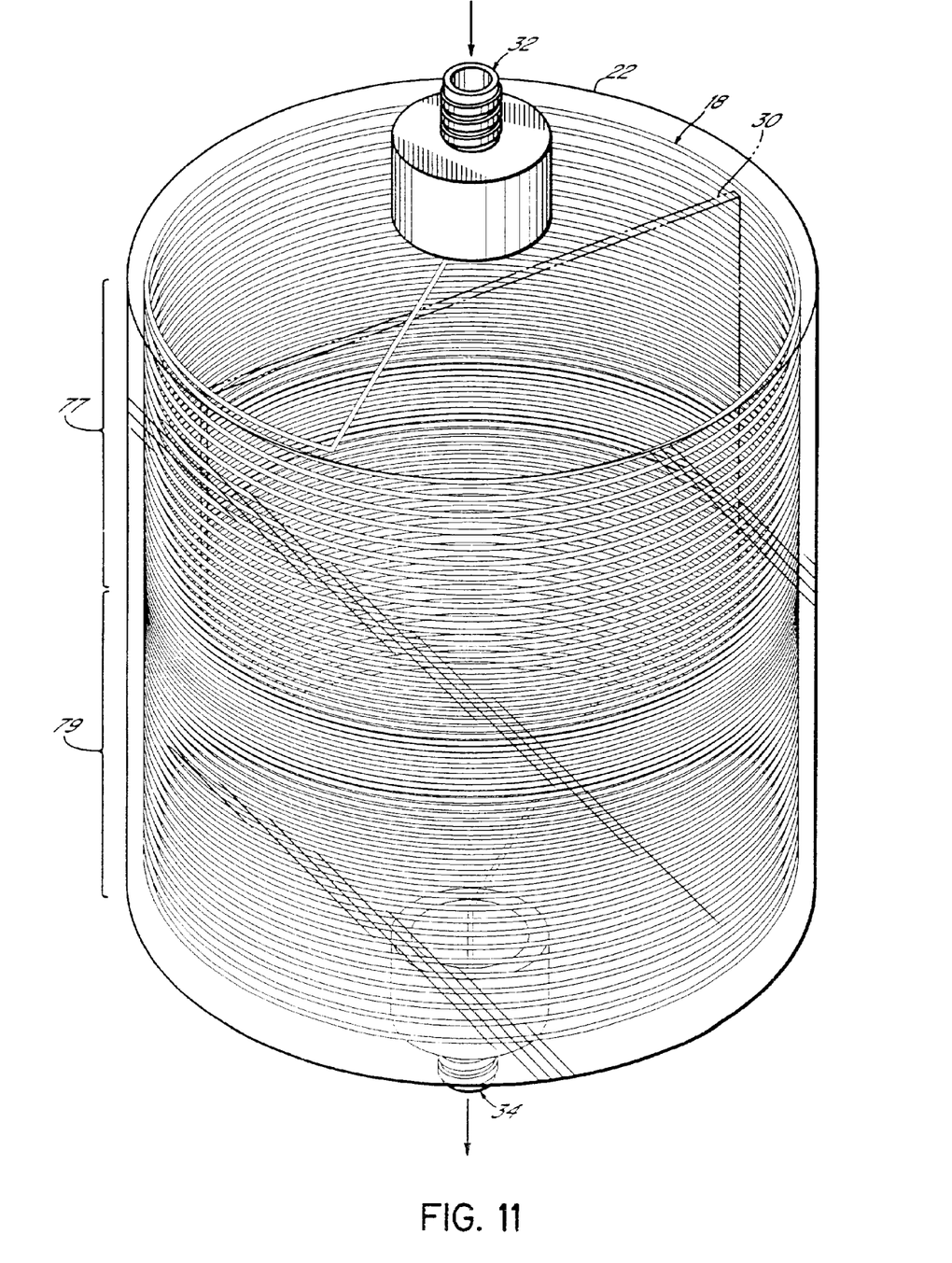
FIG. 11 is a device having a symmetrically variable tubular network.

FIG. 11 shows a further embodiment of a device with densely packed tubes 18 which have a systematically varied radius of curvature, which is mathematically defined as 1/radius with a perfect circle, or 1/radius of a best fit circle at any point of a curve. For example, a circle having a diameter of one inch has a higher radius of curvature than a circle having a diameter of one foot. The tubes 18 may or may not be wound around a fixture 30 shown in phantom. The tubular network 18, whereby the first half 77 of the network 8 is paralleled in the second half 79 of the network 8. In the first half 77 of the network 18, the radius of curvature of the tubes 18 has a density which increases from the inflow portion 32 to the center. In the second half 79 of the network, the radius of curvature of the tubes 18 has a density which decreases from the center to the outflow portion 34. An advantage of this arrangement is that irregularities in the network promote turbulence induced interlaminar mixing.

The network may be configured to be of a relatively low or high density, depending upon the outcome to be attained. A low density network is one having a relatively smaller network volume of contained agent per defined area, in contrast to a high density network, which is one having a relatively greater network volume of contained agent in the same defined area. For example, in a tubular network, tubes that are of identical sizes may be configured to have a smaller radius of curvature (for example, a radius of curvature of ⅛ inch) around a fixture. This would result in greater mixing of a contained agent than tubes 18 configured to have a larger radius of curvature (for example, a radius of curvature of one inch) around a fixture having the same internal channel geometry. This is because the agent flowing through a ⅛ inch tubular network is exposed to a greater centrifugal force in negotiating a greater number of curves than an agent flowing through a one inch tubular network.

Enhanced mixing may also be achieved by other means, for example, by altering the diameter of the channels through which the agent flows in the network, altering the pitch of grooves (that is, the distance between repairing turns on a line drawn parallel to a helical axis) in a symmetrical or partially symmetrical network configuration, and/or altering the length of the tubular network. A longer, thinner tubular network has a higher ambient pressure than a shorter wider network having the same total area. If an agent contains microbubbles suspended in a liquid, this configuration impacts the hydrostatic pressure to which the microbubbles are exposed, which in turn affects the microbubble size distribution infused into a patient. The following example, not shown in the figures, illustrates this concept.

A total volume of 1.5 ml of a microbubble-containing agent is contained in a tube having a cross-section of 0.015 inch, and wound as tightly as possible (that is, at relatively high density) around a ⅛ inch diameter rod-shaped fixture that is two feet long (that is, a total of two feet of wound tubing). If the agent is viscous, the agent will have to be subjected to increased pressure (overpressured) to flow through the tubular network. However, overpressurization collapses microbubbles of all sizes in the agent, and once the smallest sized microbubbles collapse, there is no nucleation site for exchange of the gas contained within the microbubbles. Since these smallest sized microbubbles cannot be regenerated, they are permanently removed from the agent under these conditions.

In comparison, a total volume of 6 ml of a microbubble-containing agent is contained in a tubular network having a cross-section of 0.034 inch, and wound as tightly as possible (that is, at relatively high density) around a ³⁄₁₆ inch diameter rod-shaped fixture that is two feet long (that is, a total of two feet of wound tubing). Under these conditions, even if the agent is viscous, the agent will not have to be subjected to increased pressure (overpressured) to flow through this network. Thus, no microbubbles will be collapsed and an agent containing microbubbles of all sizes will be delivered and infused into the patient.

There is, however, a trade-off between the length of the network and the cross section of the network that is independent of the volume contained. While one can obtain any volume desired if the cross-section of the network is increased sufficiently, once the cross-section is increased above a certain point, the microbubbles become trapped or hung up in the network and hence do not reach the patient.

Figure 8A:
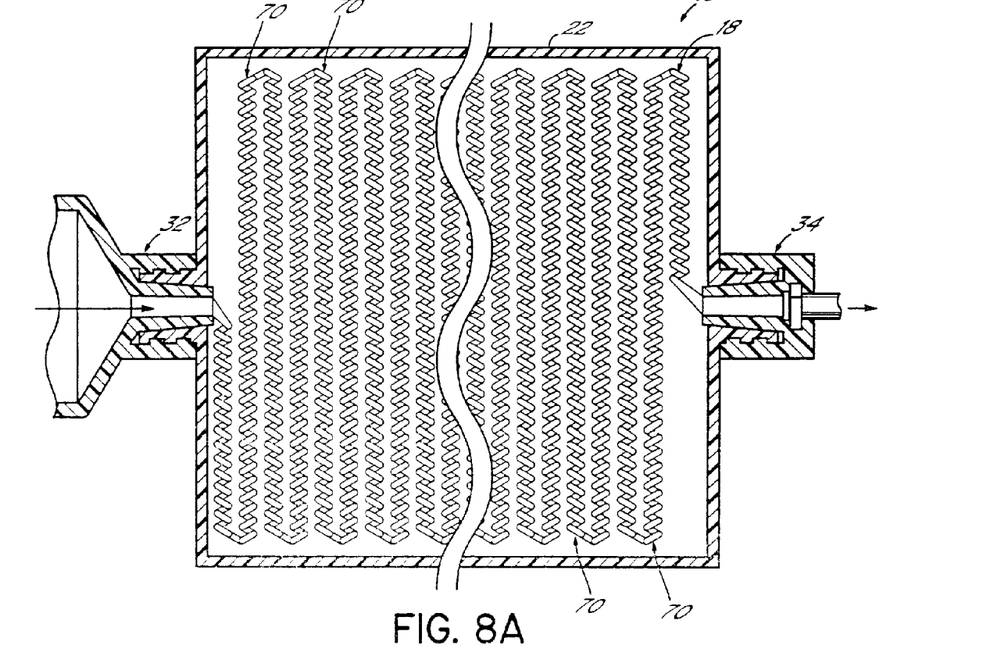
FIGS. 8A and 8B are schematics of in-line devices with tubular networks in parallel arrangements of columns.
Figure 8B:
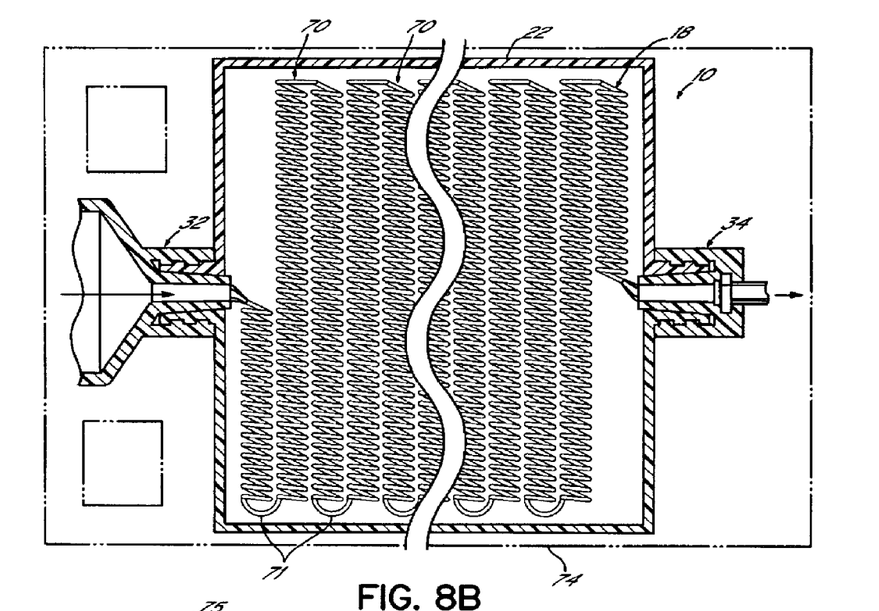
Figures 9, 10:
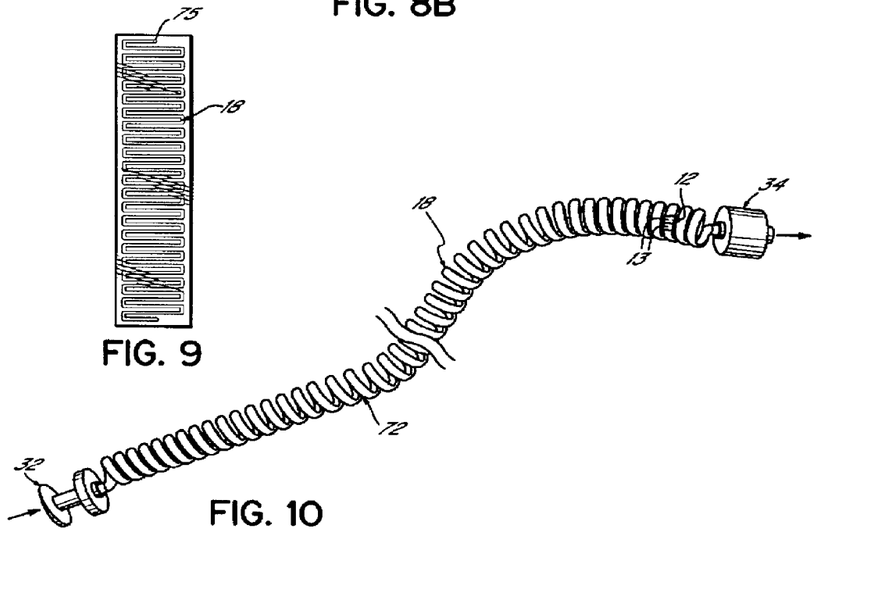
FIG. 9 is a single column removed from a device.
FIG. 10 is an in-line device with a helical tubular network.

In other embodiments, the composition of the tubular network 18 and/or network holder 22 may be altered to achieve a desired effect. For example, the network 18 and/or network holder 22 may be made of a material that protects a gaseous agent 12 contained in the network 18 from a gaseous exchange, and hence protects the integrity of the agent 12. An example of this would be a network 18 composed of a material that is less permeable or even impermeable to gas, thus decreasing gas exchange. As an alternate example, the network 18, either of a typical material or a material that is less permeable or impermeable to gas exchange, may be packaged in a secondary container 74, as shown in phantom in FIG. 8A, that is less permeable or impermeable to gas exchange, to achieve the same or similar effect. This would increase protection for agents which are sensitive to air. The secondary container 74 may be glass or a thick walled (greater than ¼ inch) plastic such as polyvinyl chloride (PVC), polypropylene, or other material that may be sterilized using gamma irradiation. Alternatively, one secondary container 74 may contain a plurality of less expensive but gas permeable containers (multi-unit packaging). This advantageously provides a secondary container 74 that is less permeable or impermeable to gas exchange, but reduces the expense of providing such a container 74 for each network 18 or network holder 22. In still another embodiment, a secondary container 74 may itself contain a gas that is the same as, or compatible with, the gas contained in the microbubbles to further decrease gas exchange and to maintain integrity of a gaseous agent, such as a microbubble-containing agent 12.

Another embodiment of the invention is the use of an inventive resuspension device in combination with a mechanical resuspension device such as a mixing apparatus (not shown). This may be advantageously used when a tubular network is being filled with an agent, for example, when a non-prefilled network embodiment is used. This embodiment may also be used when filling must occur over a period of time, during which the agent may come out of suspension, and the user desires to maintain the agent in a suspended state throughout the filling process. Additionally, this embodiment may be used when a very large volume of agent is to be delivered to a patient and the volume of agent exceeds the capacity of the network, necessitating a volume greater than the network capacity. In this case, a mechanical suspension device may be used that is small enough to be proximal to an infusion site in a patient, for example, that is taped to a patient's arm or leg, to maintain suspension of agent.

The device may be used to control the rate of delivery of sedimenting agents such as pharmaceutical colloids to a patient. Heretofore, it was not appreciated that altering the flow rate of a microbubble-containing agent would alter the normal size-distribution curve of the microbubbles in the volume of agent, and hence would alter the size distribution of the contained microbubbles that are delivered into a patient. If the agent is comprised of a plurality of microbubbles, such as a contrast agent containing a plurality of microbubbles suspended in a liquid, the rate at which the agent is delivered may be used to control the size of microbubbles that are injected into the patient. This advantageously excludes microbubbles that are above a set threshold size, which may have deleterious effects if they are injected into a patient. Also, depending upon the type of imaging procedure that a patient is to undergo and the particular organ or tissue to be imaged, infusion of microbubbles limited to a certain size range is desirable. As one example, in renal, hepatic and ocular imaging, only relatively small microbubbles in the range of about 2 $\mu$m to 4 $\mu$m should be administered, due to the small microvascular network in the kidney, liver, and eye, respectively. As another example, the clinician or technician is able to alter the microbubble size and distribution to achieve, for example, an altered backscatter or an altered attenuation. This permits the technician or clinician to make fine adjustments to the image in real time, that is, as the imaging is in progress and during infusion of the agent into the patient. As the image is being displayed and evaluated, alteration of the image quality by alteration of the delivery rate will result in images of higher diagnostic significance, and hence the imaging procedure will be of a higher diagnostic value and be more cost- and time-efficient.

This would be applicable for use in a single bolus injection of a microbubble-containing agent, as well as a continuous infusion of agent.

Control of the rate at which the agent is delivered, resulting in control of the particle size of microbubbles in an agent, is accomplished by altering the cross sectional geometry of the tubular network. Using the inventive device, the technician or clinician thus controls the profile of shear forces and mixing turbulence of the agent within the network. This impacts the hydrostatic pressure on the microbubbles, which in turn alters the flow rate of the agent through the network and in turn affects the size distribution of microbubbles reaching the infusion site and being injected into the patient.

The pressure at which the agent containing microbubbles flows through the network may also be controlled to achieve altered size distribution. Since microbubbles flow through the network at a defined hydrostatic pressure, alteration of the ambient hydrostatic pressure, either by constant or variable alteration, exposes the microbubbles to a different hydrostatic pressure at any given time.

It should be understood that the embodiments of the present invention shown and described in the specification are exemplary embodiments contemplated by the inventor and are not limiting in any way. For example, the invention is not limited to use in the clinical area and may be used in research applications, as well as in other industries where uniformly suspended agents are needed, such as the food and beverage industries. In such cases, for example, the propellant fluids 16 may also include oils, epoxy resins, sugars, etc., depending upon the application. Therefore, various changes, modifications or alterations to these embodiments may be made or resorted to without departing from the spirit of the invention and the scope of the following claims.

What is claimed is:

1. A suspension device for a physiologic injectable agent comprising:

a compressible tubular network having a plurality of helices containing a plurality of sub-volumes of a physiologic injectable suspendable contrast agent with at least two of the helices compressibly secured fastening the at least two helices together to prevent tangling of the helices, an inlet to the tubular network adapted to receive a propellant fluid flowing through the helices in contact with the agent to release sub-volumes of the contrast agent, and an outlet from the tubular network for the propellent fluid and suspended contrast agent.

2. The suspension device of claim 1 wherein the helices are secured by fastening at least one helix to at least one adjacent helix.

3. The suspension device of claim 1 wherein the helices are secured by containment in a sleeve.

4. The suspension device of claim 1 wherein the helices are fastened by a mechanical fastener, an adhesive fastener, and combinations thereof.

5. The suspension device of claim 4 wherein the mechanical fastener is selected from the group consisting of a clip, a pin, a clamp, a band, a tie, and combinations thereof.

6. The suspension device of claim 4 wherein the adhesive fastener is selected from the group consisting of tape, glue, plastic wrap, and combinations thereof.

* * * * *

UNITED STATES PATENT AND TRADEMARK OFFICE
CERTIFICATE OF CORRECTION

PATENT NO. : 6,770,051 B2
DATED : August 3, 2004
INVENTOR(S) : Hughes et al.

It is certified that error appears in the above-identified patent and that said Letters Patent is hereby corrected as shown below:

Title page,
Item [63], Related U.S. Application Data, delete the words "and a continuation" after 2000, and add -- now pending, which is a continuation-in-part of application No. 09/316,315, filed May 21, 1999, now U.S. Pat. No. 6,554,792; continuation-in-part of International --
*Primary Examiner*, change "Loan" to -- LoAn --.

Column 1,
Lines 6-7, delete the words "and is a continuation" after the word "pending" and add -- which is a continuation-in-part of application No. 09/316,315, filed May 21, 1999, now U.S. Pat. No. 6,554,792; this application is also a continuation-in-part of International Application No. --

Column 4,
Line 13, change "," after the word "flow" to -- . --.

Column 6,
Line 43, change the word "are" to -- is --.

Column 7,
Line 27, change the word "are" to -- is --.
Line 47, change "8frespectively" to -- 8f respectively --.

Column 12,
Line 23, change "," to -- . --.

Column 13,
Line 16, change the second occurrence of the word "to" after the word "secured" to -- or --.

UNITED STATES PATENT AND TRADEMARK OFFICE
CERTIFICATE OF CORRECTION

PATENT NO. : 6,770,051 B2
DATED : August 3, 2004
INVENTOR(S) : Hughes et al.

It is certified that error appears in the above-identified patent and that said Letters Patent is hereby corrected as shown below:

Column 16,
Line 15, change the word "inventor" to -- inventors --.

Signed and Sealed this

Twenty-sixth Day of April, 2005

JON W. DUDAS
*Director of the United States Patent and Trademark Office*